(12) United States Patent
Ashe et al.

(10) Patent No.: US 11,612,086 B2
(45) Date of Patent: *Mar. 21, 2023

(54) SELF-CONTAINED ELECTROMAGNETIC TRACKING UNIT

(71) Applicant: Northern Digital Inc., Waterloo (CA)

(72) Inventors: Westley S. Ashe, Hinesburg, VT (US); Richard van Wijngaarden, Waterloo (CA); Andrew Wiles, Waterloo (CA)

(73) Assignee: Northern Digital Inc., Waterloo (CA)

( * ) Notice: Subject to any disclaimer, the term of this patent is extended or adjusted under 35 U.S.C. 154(b) by 92 days.

This patent is subject to a terminal disclaimer.

(21) Appl. No.: 17/332,395

(22) Filed: May 27, 2021

(65) Prior Publication Data
US 2021/0337708 A1   Oct. 28, 2021

Related U.S. Application Data

(63) Continuation of application No. 16/242,765, filed on Jan. 8, 2019, now Pat. No. 11,076,511.

(51) Int. Cl.
| | | |
|---|---|---|
| *H05K 9/00* | (2006.01) | |
| *H05K 1/02* | (2006.01) | |
| *H01F 17/04* | (2006.01) | |
| *H01F 27/24* | (2006.01) | |
| *H01F 27/28* | (2006.01) | |
| *H01F 27/32* | (2006.01) | |

(Continued)

(52) U.S. Cl.
CPC .......... *H05K 9/0022* (2013.01); *A61B 34/20* (2016.02); *A61B 90/37* (2016.02);
(Continued)

(58) Field of Classification Search
CPC .... G01R 33/00; G01R 33/02; G01R 33/0206; H01F 17/00; H01F 17/04; H01F 27/00;
(Continued)

(56) References Cited

U.S. PATENT DOCUMENTS

| | | |
|---|---|---|
| 4,611,169 A | 9/1986 | Hermann |
| 4,695,795 A | 9/1987 | Nakamizo et al. |

(Continued)

FOREIGN PATENT DOCUMENTS

| | | |
|---|---|---|
| CA | 2836019 | 6/2014 |
| CN | 102036466 | 4/2011 |

(Continued)

OTHER PUBLICATIONS

International Preliminary Report on Patentability in International Appln. No. PCT/US2020/012540, dated Jul. 22, 2021, 7 pages.

(Continued)

*Primary Examiner* — Hoai-An D. Nguyen
(74) *Attorney, Agent, or Firm* — Fish & Richardson P.C.

(57) ABSTRACT

An electromagnetic tracking system includes a magnetic transmitter configured to output magnetic fields, a receiver responsive to the magnetic fields, an electronics assembly having conductive elements that cause distortion to the magnetic fields, and an output mechanism configured to output a position of the receiver relative to the magnetic transmitter, wherein the magnetic transmitter has at least one winding disposed around a hollow ferromagnetic core comprised of conductive material through which current is made to flow by the electronics, wherein the electronics assembly is at least partially contained within the hollow portion of the hollow ferromagnetic core. Methods of manufacturing include shaping walls into a hollow shell to surround an electronics assembly, covering the hollow shell with ferromagnetic material, inserting the wrapped hollow shell into a plastic bobbin, and winding the plastic bobbin with coil wire to produce three orthogonal windings.

20 Claims, 5 Drawing Sheets

(51) Int. Cl.
*H01F 41/061* (2016.01)
*G01R 33/02* (2006.01)
*A61B 34/20* (2016.01)
*A61B 90/00* (2016.01)
*A61B 90/50* (2016.01)

(52) U.S. Cl.
CPC ......... *G01R 33/0206* (2013.01); *H01F 17/04* (2013.01); *H01F 27/24* (2013.01); *H01F 27/2823* (2013.01); *H01F 27/325* (2013.01); *H01F 41/061* (2016.01); *H05K 1/028* (2013.01); *H05K 9/0043* (2013.01); *A61B 2034/2051* (2016.02); *A61B 2034/2072* (2016.02); *A61B 2090/502* (2016.02)

(58) Field of Classification Search
CPC ...... H01F 27/24; H01F 27/28; H01F 27/2823; H01F 27/32; H01F 27/324; H01F 27/325; H01F 41/00; H01F 41/02; H01F 41/04; H01F 41/06; H01F 41/061; A61B 34/00; A61B 34/20; A61B 2034/2051; A61B 2034/2072; A61B 90/00; A61B 90/36; A61B 90/37; A61B 90/50; A61B 2090/502
USPC ........... 324/200, 207.11, 207.22, 76.11, 144; 340/500, 540, 541, 545.1, 545.2, 545.3, 340/531, 539.1, 539.11, 539.13; 361/139, 361/159; 701/400, 408, 519; 702/1, 33, 702/35, 38
See application file for complete search history.

(56) References Cited

U.S. PATENT DOCUMENTS

| | | |
|---|---|---|
| 4,812,812 A | 3/1989 | Flowerdew et al. |
| 7,835,779 B2 | 11/2010 | Anderson et al. |
| 9,964,567 B2 | 5/2018 | Meehleder |
| 11,076,511 B2 | 7/2021 | Ashe et al. |
| 2005/0140487 A1 | 6/2005 | Sippola et al. |
| 2005/0288743 A1 | 12/2005 | Ahn et al. |
| 2013/0141081 A1 | 6/2013 | Pfaffinger et al. |
| 2015/0115944 A1 | 4/2015 | Ashe |
| 2016/0009166 A1 | 1/2016 | Sassi et al. |
| 2017/0135602 A1 | 5/2017 | Izmirli et al. |
| 2017/0241808 A1 | 8/2017 | Muratov et al. |
| 2018/0025824 A1 | 1/2018 | Kraemer et al. |
| 2019/0025040 A1 | 1/2019 | Andreason |
| 2019/0164680 A1 | 5/2019 | Cobos Reyes et al. |
| 2020/0221612 A1 | 7/2020 | Ashe |

FOREIGN PATENT DOCUMENTS

| | | |
|---|---|---|
| EP | 1806756 | 7/2007 |
| JP | 2007184618 | 7/2007 |
| TW | 201417638 | 5/2014 |
| WO | WO 1988/09479 | 12/1988 |
| WO | WO 2007/009088 | 1/2007 |

OTHER PUBLICATIONS

PCT International Search Report and Written Opinion in International Appln. No. PCT/US2020/012540, dated May 15, 2020, 10 pages.

SELF-CONTAINED ELECTROMAGNETIC TRACKING UNIT

CROSS-REFERENCE TO RELATED APPLICATIONS

This application is a continuation application of and claims priority to U.S. application Ser. No. 16/242,765, filed on Jan. 8, 2019.

TECHNICAL FIELD

This invention relates to a self-contained electromagnetic tracking unit.

BACKGROUND

To improve field strength, wire coils used in electromagnetic (EM) tracking systems are wrapped around a ferromagnetic core. The resulting assemblage is heavy and requires a separate connection to external drive circuitry and signal processing.

SUMMARY

Electronics in an EM tracking unit must be shielded from the magnetic fields developed by the wire windings (or coils) disposed around their ferromagnetic cores. New, light core materials have become available, permitting EM units to be cored out, and even to be completely hollow. The EM tracking unit transmitter described herein makes use of the now-available empty space inside the core to contain all necessary drive circuitry for the coil. The coil drive circuitry is contained within the core for a combined smaller and lighter unit compared with previous units while being shielded with a ferromagnetic layer. The shielding reduces the distortion of the magnetic fields developed by the winding disposed around the hollow ferromagnetic core. This reduced distortion improves the accuracy of the position output from the electromagnetic tracker.

In some embodiments, an electromagnetic tracking system includes a magnetic transmitter configured to output magnetic fields, a receiver responsive to the magnetic fields, an electronics assembly having conductive elements that cause distortion to the magnetic fields, and an output mechanism configured to output a position of the receiver relative to the magnetic transmitter, wherein the magnetic transmitter has at least one winding disposed around a hollow ferromagnetic core comprised of conductive material through which current is made to flow by the electronics, wherein the electronics assembly is at least partially contained within the hollow portion of the hollow ferromagnetic core.

Implementations may include one or more of the following features. The electronics assembly is entirely contained within the hollow portion the hollow ferromagnetic core. The hollow ferromagnetic core comprises a flexible ferromagnetic material. The flexible ferromagnetic material comprises fabric. The ferromagnetic core comprises an adhesive layer and a backing layer attached to the fabric. The electronics assembly is printed on a flexible circuit that is contained within the hollow portion of the ferromagnetic core. A plastic bobbin surrounds the flexible circuit. The flexible circuit has folding features that allow the flexible circuit to be folded into a cuboid shape. The folding features define wall portions and a central support portion. The central support portion is configured to rest against two of the wall portions. The hollow ferromagnetic core comprises a rigid ferromagnetic material. The rigid ferromagnetic material is formed ferrite. The rigid ferromagnetic material is a sintered ferrite/binder composite.

In some embodiments, a method of manufacturing a magnetic transmitter, the method including shaping walls into a hollow shell to surround an electronics assembly, covering the hollow shell with ferromagnetic material, inserting the wrapped hollow shell into a plastic bobbin, and winding the plastic bobbin with coil wire to produce three orthogonal windings.

Implementations may include one or more of the following features. The walls comprise a flexible circuit including the electronics assembly and shaping the walls comprises folding the flexible circuit into portions including a central portion and four wall portions. Shaping walls into a hollow shell comprises supporting an edge of the central portion between two wall portions. Shaping walls into a hollow shell comprises folding a flexible circuit with the electronics assembly on a side of the flexible directed towards an interior of the hollow shell. Shaping a hollow shell circuit comprises folding a flexible circuit into a cuboid shape. Covering the hollow shell comprises wrapping a rigid sintered ferrite material around the hollow shell.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system can be used in gaming and/or surgical settings to track devices (e.g., gaming controllers, head-mounted displays, medical equipment, robotic arms, etc.), thereby allowing their respective three-dimensional positions and orientations to be known to a user of the system. Augmented Reality (AR) and Virtual Reality (VR) systems also use EMT systems to perform head, hand, and body tracking, for example, to synchronize the user's movement with the AR/VR content. Such EMT systems use a magnetic transmitter in proximity to a magnetic sensor to determine the position and/or orientation of the sensor relative to the transmitter. Sensors used in such a system provide accurate position and orientation information to the medical professional.

Figure 1A:
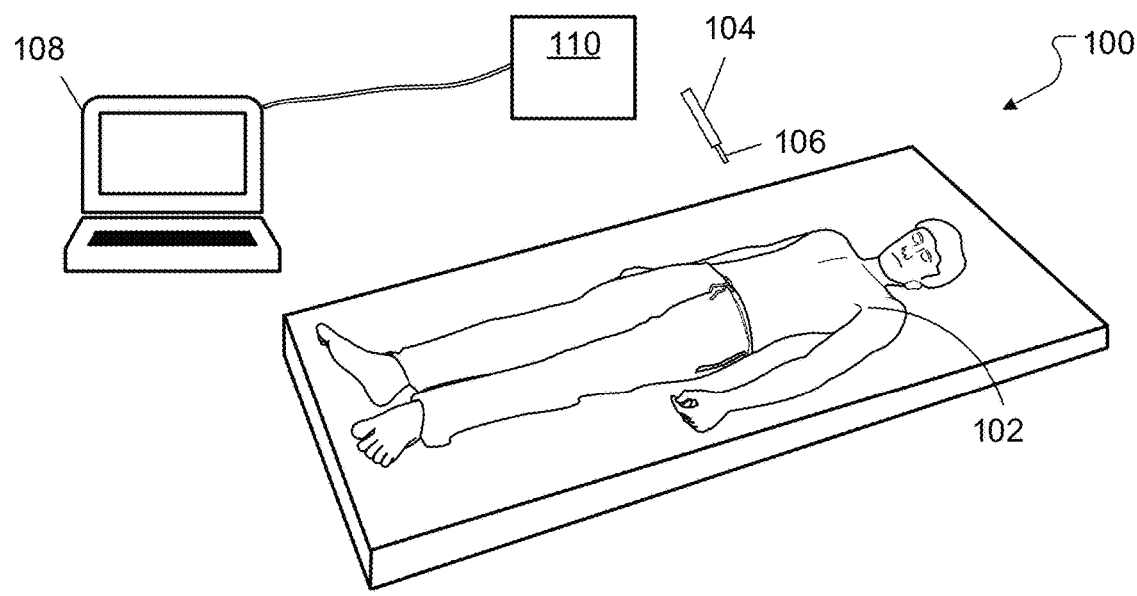
FIG. 1A is an exemplary embodiment of an Electromagnetic Tracking (EMT) system.

FIG. 1A is an exemplary embodiment of an EMT system 100, which can be used for image-guided medical procedures performed on a patient 102, for example. The system 100 may include a freely moving medical instrument 104, which can include any manner of surgical tools and devices for use in medical treatment. The system 100 permits targeting of an anatomical organ, structure, vessel, etc. for visualization, diagnostic, interventional purposes, etc.

Instruments for use in the EMT system 100 may include one or more magnetic sensors including one or more coils. For example, the instrument 104 may include a three-axis sensor 106 that includes a concentric, collocated set of sensors coils. The sensor 106 may be embedded in a channel, affixed to a tip, etc. of the instrument 104. The particular sensor employed by the system 100 may be determined by the procedure type and/or the measurement performance requirements. The sensor 106 is connected to a computing device (e.g., a computer 108).

Under control of circuitry for energizing magnetic fields, the sensor 106 measures its instantaneous position (x, y, z) and orientation angles (azimuth, altitude, roll) in three-dimensional space referenced to a transmitter 110. Like the sensor 106, the particular transmitter 110 employed by the system 100 may be determined by the procedure type, measurement performance requirements, etc. In some implementations, the transmitter 110 may be a three-axis transmitter that includes a concentric, collocated set of transmitter coils. The transmitter 110 is typically fixed in space beside, above, or beneath the patient or on medical equipment, where it acts as a spatial reference frame for the measurements provided by the sensor 106.

In some implementations, the computer 108 is an imaging computer that is configured to provide imaging capabilities to the system 100. The imaging computer 108, which can be in wired or wireless communication with the sensor 106 and transmitter 110, is configured to store pre-acquired or intra-operative images of the patient 102 in an image database. Such images may then be input to imaging software for registration and visualization purposes. During the medical procedure, the three-dimensional location of the instrument 104 can be tracked relative to the anatomy of the patient 102 and the pre-acquired or inter-operative images are presented in real time on a display of the computer 108. When the instrument 104 advances toward the target of interest within the body of the patient 102, the transmitter 110 can be activated and energized, thus producing electromagnetic signals that are sensed by the senor 106 and represented as signals (e.g., voltage signals). These signals are processed and the three-dimensional location is computed for transmission to the computer 108. In some implementations, the computer 108 includes a guidance electronics unit that is configured to process the voltage signals\to provide the three-dimensional location.

Figure 1B:
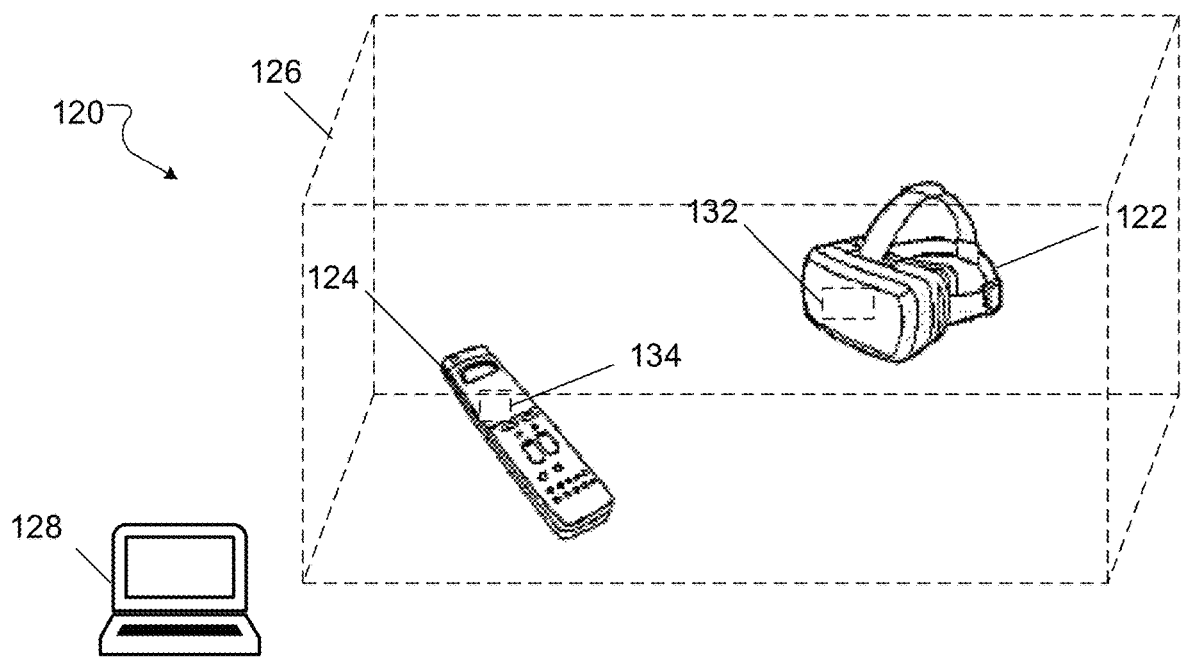
FIG. 1B shows another example of an EMT system.

FIG. 1B shows another example of an EMT system 120 that can be used as part of a VR/AR or other system (e.g., a medical system such as in FIG. 1A, or a gaming system). The EMT system 120 includes a head-mounted display (HMD) 122 that includes a magnetic sensor 132 and a controller 124 that includes a magnetic transmitter 134. The HMD 122 and the controller 124 are configured to track position and orientation in three-dimensional space relative to each other. For example, the transmitter 134 of the controller 124 is configured to track the sensor 132 of the HMD 122 relative to a reference frame defined by the position and orientation of the transmitter 134, or the sensor 132 of the HMD 122 is configured to track the transmitter 134 of the controller 124 relative to a reference frame defined by the position and orientation of the sensor 132. The particular sensor 132 and transmitter 134 employed by the EMT system 120 may be determined by the process for which it is being used, measurement performance requirements, etc.

The position and orientation of the HMD 122 and the controller 124 can be tracked relative to each other within a tracking volume 126. While the tracking volume 126 is illustrated as being a defined space, it should be understood that the tracking volume 126 may be any three-dimensional space, including dimensionless three-dimensional spaces (e.g., large indoor and/or outdoor areas, etc.).

In some implementations, the transmitter 134 includes three orthogonally wound magnetic coils, referred to herein as the x, y, and z coils. Electrical currents traveling through the three coils cause the coils to produce three orthogonal magnetic fields at three frequencies (e.g., three different frequencies) for FDM (frequency division multiplexing) applications or three pulses (e.g., three different time slots) for TDM (time division multiplexing) applications. The three frequencies may be three closely spaced frequencies, e.g., 34 KHz, 34.25 KHz, and 34.5 KHz, although other frequencies can also or alternatively be used. In some implementations, the coils may produce magnetic fields at the same frequency but, for example, used in a TDM fashion. The sensor 132 also includes three orthogonally wound magnetic coils, referred to herein as the x, y, and z coils. Voltages are induced in the coils of the sensor 132 in response to the sensed magnetic fields by magnetic induction. Each coil of the sensor 132 generates an electrical signal for each of the magnetic fields generated by the coils of the transmitter 134; for example, the x coil of the sensor 132 generates a first electrical signal in response to the magnetic field received from the x coil of the transmitter 134, a second electrical signal in response to the magnetic field received from the y coil of the transmitter 134, and a third electrical signal in response to the magnetic field received from the z coil of the transmitter 134. The y and z coils of the sensor 132 similarly generate electrical signals for each of the magnetic fields received from each coil of the transmitter 134. The sensor may also include other sensing elements that measure magnetic fields, e.g., Hall effect elements, etc.

The data from the sensor 132 can be represented as a matrix of data (e.g., a 3×3 matrix), which can be resolved into the position and orientation of the sensor 132 with respect to the transmitter 134, or vice versa. Electronics incorporated into the HMD 122 are configured to determine the position and orientation of the controller 124 relative to the HMD 122 based on the characteristics of the magnetic fields generated by the transmitter 134 and the various electrical signals generated by the sensor 132. As described above, a computer system 128 may also be configured to determine the position and orientation of a sensor and/or a transmitter.

The electronics within an EM tracking unit such as transmitter 110 or transmitter 134 must be shielded from the magnetic fields developed by the wire windings disposed around the core of the units. New, light core materials have become available, permitting EM transmitter units to be cored out, and even to be completely hollow. The EM transmitter described herein makes use of the empty space inside the core to contain all necessary drive circuitry for the surrounding coils. The coil drive circuitry is contained within the coil for a combined smaller and lighter unit compared with previous units and is shielded with a ferromagnetic layer. The shielding reduces the distortion of the magnetic fields developed by the coils disposed around the hollow core. This reduced distortion improves the accuracy of the position output from the electromagnetic tracker.

Figure 2:
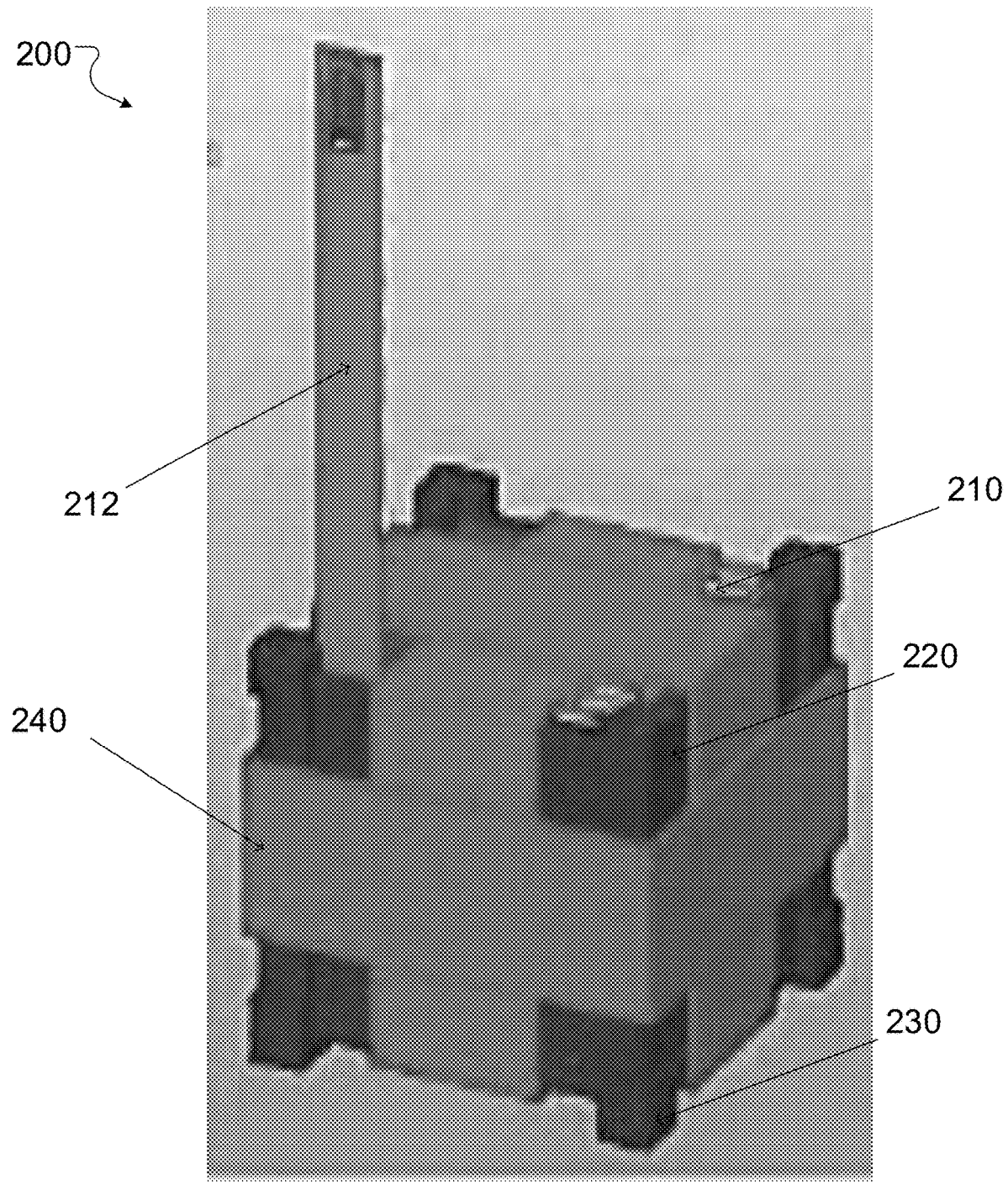
FIG. 2 is an assembled self-contained tracking unit for use with the EMT systems of FIGS. 1A and 1B.

FIG. 2 shows a tracking unit 200 that can be used as transmitter 110 or transmitter 134. The tracking unit 200 has walls that are shaped into a shell around a hollow core. The walls can be a flexible circuit 210 that is conductive and contains electronic circuitry 214 (best seen in FIGS. 3A and 3B) necessary for transmitting signals as described above. The flexible circuit 210 is folded upon itself into a cuboid configuration to provide structural rigidity for the additional components that surround the flexible circuit 210. These components include a ferromagnetic fabric material 220 that covers the flexible circuit 210, which is inserted into a plastic bobbin 230 that is wound with coil wire 240. The coil wire 240 is terminated by soldering to an exposed portion 212 of the flexible circuit 210. The coil drive circuitry 214 is thereby contained within the coil wire 240 for a compact and light unit.

Figure 3A:
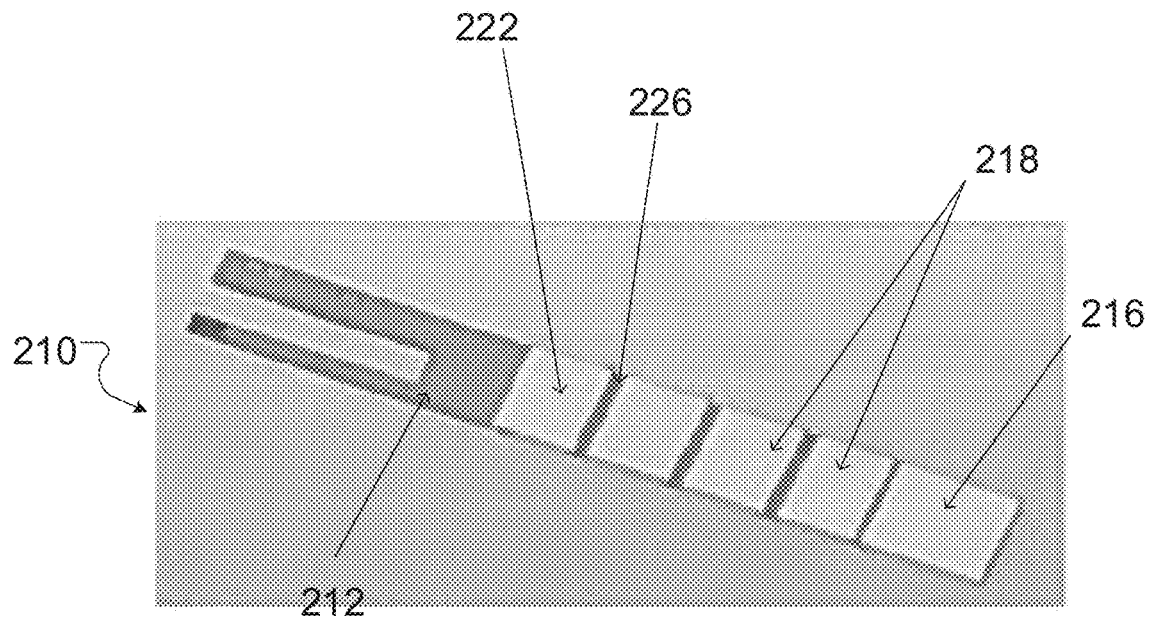
FIGS. 3A-3B are views of a flexible circuit for use with the unit of FIG. 2.
Figure 3B:
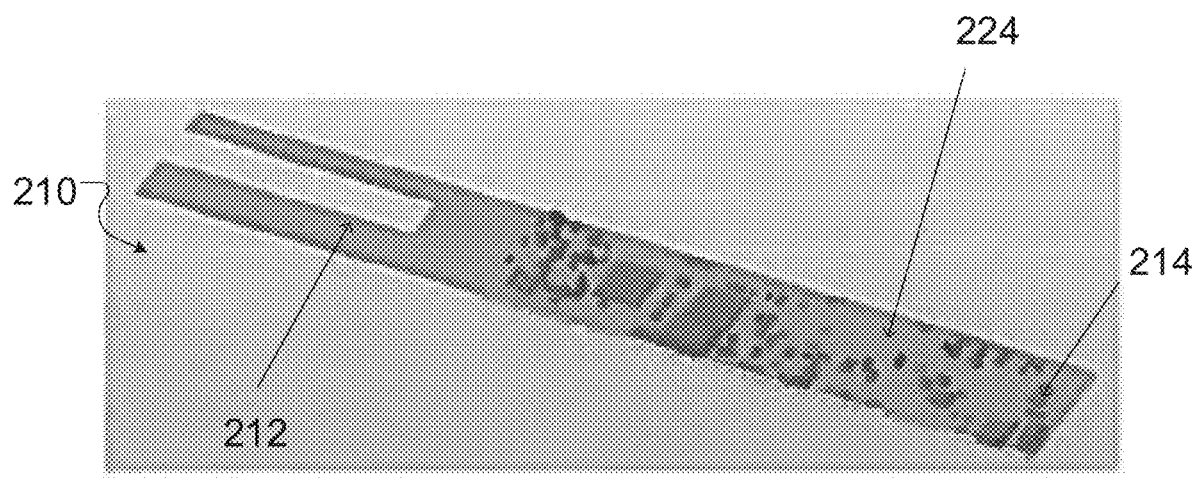

Referring to FIGS. 3A and 3B, the flexible circuit 210 includes a first side 222 and a second side 224. The first side 222 can include folding features 226 that simplify folding of the flexible circuit 210 into the desired final (e.g., cuboid) shape. These folding features 226 can be, for example, etched lines or other reduced thicknesses that allow the flexible circuit 210 to bend along the folding features 226. In the example shown, the folding features 226 divide the flexible circuit 210 into at least five portions, including central portion 216 and four wall portions 218. The second side 224 includes the electronic circuitry 214 for signal transmission. In some instances, the exposed portion 212 of the flexible circuit 210 is attached to the end of the four wall portions 218 that is opposite from the central portion 216.

Figure 4C:
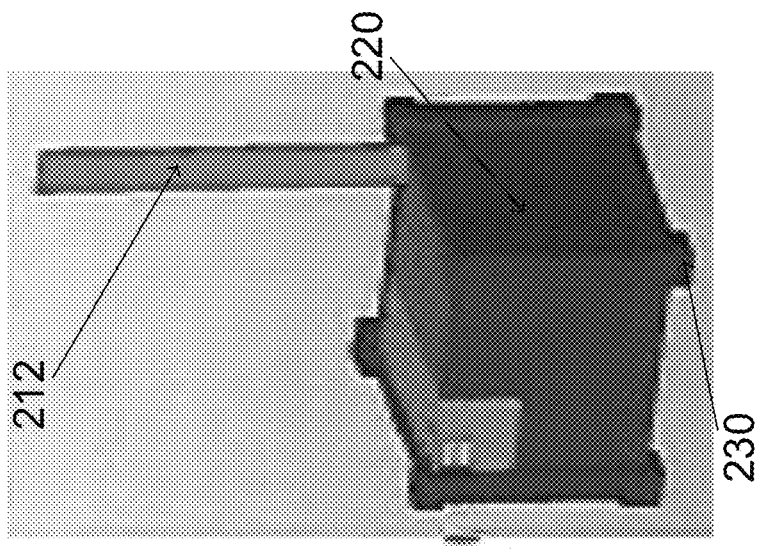
FIGS. 4A-4C are steps for manufacturing the self-contained tracking unit of FIG. 2.
Figure 4B:
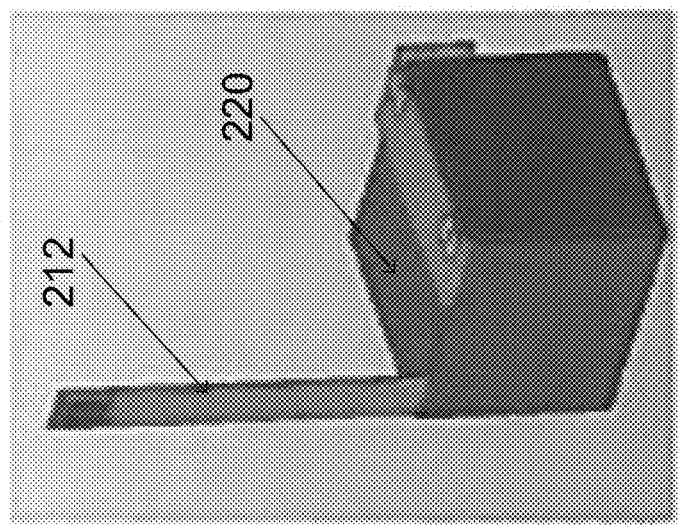
Figure 4A:
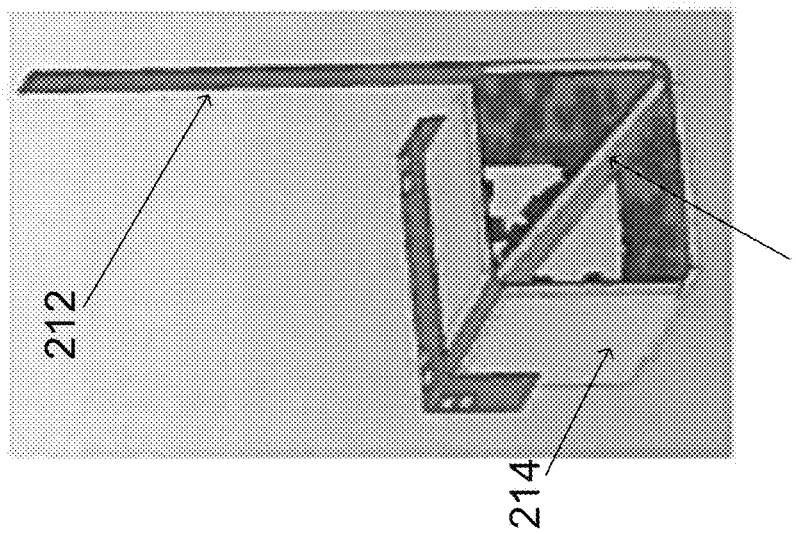

FIGS. 4A-4C illustrate the steps for forming a tracking unit 200 that can be used as transmitter 110 or transmitter 134. In FIG. 4A, the flexible circuit 210 is folded upon itself into a cuboid configuration. The second side 224 including the electronic circuitry 214 is folded such that the circuitry is directed towards the empty interior of the cube. The four wall portions 214 provide support surfaces for the additional components that surround the flexible circuit 210. The central portion 216 is bent diagonally within the four wall portions 214 to provide additional structural rigidity.

In FIG. 4B, the ferromagnetic fabric material 220 is then placed around the folded flexible circuit 210 by wrapping it around the exterior the folded circuit (e.g., the first side 222 of the folded circuit, now facing outwards from the core). The fabric material 220 can be wrapped around the circuit so as no gaps, or only small gaps are between the interior core of the folded circuit and the exterior of the fabric material remain.

The wrapped flexible circuit 210 is then inserted into a bobbin 230, FIG. 4C. The bobbin 230 holds the ferromagnetic material 220 in place around the flexible circuit 210. For low cost and ease of manufacture the bobbin can be made of plastic. The walls of the bobbin have a small thickness, sufficient to hold the fabric in place and to keep the assembly from collapsing due to the tension of the surrounding wires 240. In some instances, the order of the steps can be modified, e.g., the bobbin 230 can be placed directly around the flexible circuit 210 and subsequently covered by the ferromagnetic fabric material 220. In such arrangements the ferromagnetic fabric material 220 is mounted to the external faces of the bobbin 230.

Once the plastic bobbin 230 contains the wrapped flexible circuit, the partially-assembled unit is then wound with coil wire 240 to produce three orthogonal windings and to provide the configuration shown in FIG. 2. The thicknesses and number of windings of the coil wire are determined by the application for which the tracking unit 200 is intended. The coil drive circuitry 214 and its electronics assembly is thereby contained within the coil wire 240, and within the ferromagnetic portion of the core. The coil drive circuitry communicates with the exposed portion 212 of the flexible circuit 210 that is positioned outside of the wires 240 and the core. The result is a compact and light tracking unit 200.

The ferromagnetic fabric material 220 can include an adhesive backing layer that secures the ferromagnetic portion of the material sheet to the bobbin 230 or some other structure within the coil. Without adhesive and backing material, the ferromagnetic material can have a thickness between 0.1 and 0.3 mm. With adhesive and backing material the thickness increases by approximately 0.2 mm.

The ferromagnetic fabric material 220 can include iron, nickel, cobalt, and alloys thereof. The material can be shaped into sheets, rods, wire, or powders and applied to cover and/or surround the hollow flexible circuit 210. In some instances (e.g., with wire) the ferromagnetic component can be embedded in a non-ferromagnetic fabric.

In some embodiments, the ferromagnetic material is sintered ferromagnetic material with a suitable magnetic permeability for operation in the frequency range for the final transmitter unit. Rather than being a flexible fabric, the ferromagnetic material can be formed ferrite, having a rigid, sintered construction. The rigid, sintered material can additionally or alternatively include a ferrite/binder matrix or composite, and the formed ferrite can be formed into one or more elements conveniently arranged to form a hollow core that surrounds the transmitter circuitry. Typically, the binder is a polymer. The ferrite/binder mixture can be molded (while in liquid form) or heat formed (into a sheet or strips) around the electronics. In such arrangements, a bobbin may be dispensed with as the formed ferrite provides sufficient structural integrity to the final unit. The unit can instead have the form of an open-ended cube with or without an end cap(s) enclosing the electronics.

Instead of a ferromagnetic material, high permeability sheets or strips can be used. For example, permalloy 80 sheets (a highly magnetic nickel-iron-molybdenum alloy) is available in 0.0025 mm thicknesses; these sheets can be cut into ribbons and wound or formed in a similar manner to the ferrite fabric as described above.

The ferromagnetic transmitter core described herein is hollow, and some portion of the electronics (e.g., all of the electronics) is disposed within the hollow portion, which provides significant advantages. The ferromagnetic material shields the electronics from the magnetic fields developed by the winding disposed around the hollow ferromagnetic core. The shielding provides the advantages of reducing the distortion of the magnetic fields developed by the winding disposed around the hollow ferromagnetic core. The reduced distortion improves the accuracy of the position output from the electromagnetic tracker. At the same time, the hollow unit is light and compact, and simple to manufacture.

Figure 5:
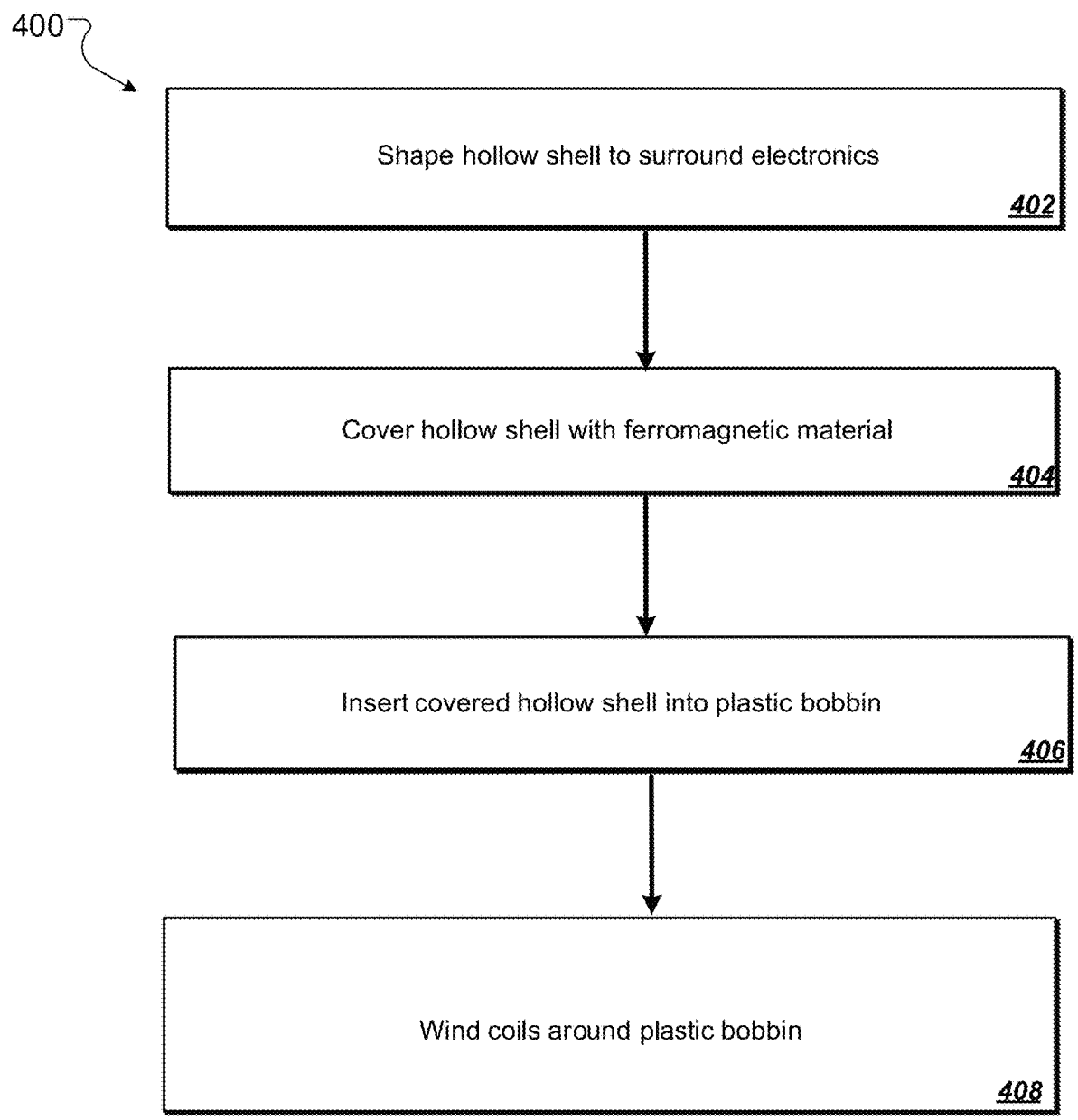
FIG. 5 is a flow chart showing steps for manufacturing the self-contained tracking unit of FIG. 2.

FIG. 5 shows the steps of a method 400 for forming a tracking unit 200 that can be used as transmitter 110 or transmitter 134. In step 402, walls are shaped into a hollow shell to surround an electronics assembly, for example by folding the flexible circuit 210 in upon itself into a cuboid configuration, with the second side 224 including the electronic circuitry 214 directed towards the hollow interior of the cube. The folding can include bending the central portion 216 within the four wall portions 214 and supporting an edge of the central portion 216 between two wall portions 214 to provide additional structural rigidity. At step 404, the hollow shell of the flexible circuit 210 is covered with ferromagnetic material such as flexible ferrite fabric material 220 by wrapping it around the flexible circuit 210 on its first side 222. At step 406, the wrapped hollow shell is then inserted into a plastic bobbin 230. The plastic bobbin is then wound with coil wire 240 to produce three orthogonal windings and to provide the final configuration, step 408.

A number of embodiments of the invention have been described. Nevertheless, it will be understood that various modifications may be made without departing from the spirit and scope of the invention.

For example, the tracking unit shown in the figures is represented as having a cuboid shape. However, other shapes are possible, e.g., non-cuboid prisms, spherical, cylindrical, etc. Thus, while the flexible circuit 210 is described as being folded into five portions, other numbers of portions are possible (e.g., less than five or more than five).

In some embodiments, instead of being folded, the flexible circuit 210 can be several different portions that are assembled together. For example, four or six wall portions may be joined together to form an open (as shown in FIG. 4A) cube or a closed cube. Such joining may be by adhesive, soldering, welding, etc. The wall portions form the walls of the hollow core and protect the circuitry in the interior.

The exposed portion 212 of the flexible circuit 210 may be integral with the flexible circuit 210, or can be separate from it. For example, the exposed portion 212 can be attachable to the remainder of the flexible circuit 210, e.g., by soldering, either prior to or following assembly of the remainder of the unit.

In some instances, the electronic circuitry 214 is located on a single portion of circuit material (e.g., one of the five portions discussed above). That portion can form a wall (with the electronics directed to the interior), or be a separate portion that is placed within (e.g., diagonally) the hollow core formed by folding flexible material without circuitry.

Accordingly, other embodiments are within the scope of the following claims.

What is claimed is:

1. A magnetic transmitter comprising:
an electronics assembly having conductive elements; and
at least one winding disposed around a hollow ferromagnetic core, the at least one winding comprised of conductive material capable of current flow by the electronics assembly, wherein the electronics assembly is at least partially contained within a hollow portion of the hollow ferromagnetic core,
wherein the electronics assembly comprises a flexible circuit contained in the hollow portion of the hollow ferromagnetic core, the flexible circuit being folded to provide structural support to a ferromagnetic material of the magnetic transmitter.

2. The magnetic transmitter of claim 1, wherein the electronics assembly is entirely contained within the hollow portion the hollow ferromagnetic core.

3. The magnetic transmitter of claim 1, wherein the ferromagnetic material comprises a flexible ferromagnetic material and the hollow ferromagnetic core comprises the flexible ferromagnetic material.

4. The magnetic transmitter of claim 3, wherein the flexible ferromagnetic material comprises fabric.

5. The magnetic transmitter of claim 4, wherein the hollow ferromagnetic core comprises an adhesive layer and a backing layer attached to the fabric.

6. The magnetic transmitter of claim 1, comprising a plastic bobbin that surrounds the flexible circuit.

7. The magnetic transmitter of claim 1, wherein the flexible circuit has folding features that allow the flexible circuit to be folded into a cuboid shape.

8. The magnetic transmitter of claim 7, wherein the folding features define wall portions and a central support portion.

9. The magnetic transmitter of claim 8, wherein the central support portion is configured to rest against two of the wall portions.

10. The magnetic transmitter of claim 1, wherein the flexible circuit is folded such that electronic circuitry of the flexible circuit is directed towards an empty interior of a folded shape of the flexible circuit.

11. The magnetic transmitter of claim 1, wherein the ferromagnetic material comprises a rigid ferromagnetic material and the hollow ferromagnetic core comprises the rigid ferromagnetic material.

12. The magnetic transmitter of claim 11, wherein the rigid ferromagnetic material is formed ferrite.

13. The magnetic transmitter of claim 11, wherein the rigid ferromagnetic material is a sintered ferrite/binder composite.

14. An electromagnetic tracking system comprising:
a magnetic transmitter configured to output magnetic fields, the magnetic transmitter comprising at least one winding disposed around a hollow core of the magnetic transmitter and a foldable circuit located within the hollow core, the foldable circuit being folded to provide structural support to a material of the magnetic transmitter, the material being located between the foldable circuit and the at least one winding; and
a receiver responsive to the magnetic fields.

15. The electromagnetic tracking system of claim 14, wherein the material comprises a flexible ferromagnetic material and the hollow core comprises the flexible ferromagnetic material.

16. The electromagnetic tracking system of claim 15, wherein the flexible ferromagnetic material comprises fabric.

17. The electromagnetic tracking system of claim 14, wherein the foldable circuit has folding features that allow the foldable circuit to be folded into a cuboid shape.

18. The electromagnetic tracking system of claim 17, wherein the folding features define wall portions and a central support portion.

19. The electromagnetic tracking system of claim 18, wherein the central support portion is configured to rest against two of the wall portions.

20. The electromagnetic tracking system of claim 14, wherein the foldable circuit is folded such that electronic circuitry of the foldable circuit is directed towards an empty interior of a folded shape of the foldable circuit.

* * * * *

UNITED STATES PATENT AND TRADEMARK OFFICE
CERTIFICATE OF CORRECTION

| | |
|---|---|
| PATENT NO. | : 11,612,086 B2 |
| APPLICATION NO. | : 17/332395 |
| DATED | : March 21, 2023 |
| INVENTOR(S) | : Westley S. Ashe, Richard van Wijngaarden and Andrew Donald Wiles |

Page 1 of 1

It is certified that error appears in the above-identified patent and that said Letters Patent is hereby corrected as shown below:

On the Title Page

Column 1, (71) Applicant:, after "Waterloo" insert --ON--.

In the Specification

Column 7, Line 52, after "portion" insert --of--.

Signed and Sealed this
Twentieth Day of June, 2023

*Katherine Kelly Vidal*

Katherine Kelly Vidal
*Director of the United States Patent and Trademark Office*